United States Patent [19]

Forsberg

[11] Patent Number: 4,774,351

[45] Date of Patent: Sep. 27, 1988

[54] AQUEOUS FLUIDS COMPOSITIONS CONTAINING DITHIOPHOSPHORUS/AMINE SALTS

[75] Inventor: John W. Forsberg, Mentor-On-The-Lake, Ohio

[73] Assignee: The Lubrizol Corporation, Wickliffe, Ohio

[21] Appl. No.: 117,728

[22] Filed: Nov. 6, 1987

Related U.S. Application Data

[62] Division of Ser. No. 456,219, Jan. 7, 1983, Pat. No. 4,721,802.

[51] Int. Cl.$^4$ .............................................. C07S 9/115
[52] U.S. Cl. ..................................................... 558/207
[58] Field of Search ..................... 558/207; 260/501.21

[56] References Cited

U.S. PATENT DOCUMENTS

| | | | |
|---|---|---|---|
| 2,737,492 | 3/1956 | Beegle et al. | 252/32.7 |
| 2,894,951 | 7/1959 | Millikan et al. | 260/925 |
| 3,002,014 | 9/1981 | Dinsmore et al. | 260/461 |
| 3,058,910 | 10/1962 | Culmer | 252/32.7 |
| 3,103,492 | 9/1963 | Dinsmore et al. | 252/32.7 |
| 3,124,556 | 3/1964 | Merrifield et al. | 260/925 |
| 3,201,447 | 8/1965 | Cyba | 260/461 |
| 3,320,164 | 5/1967 | Brunel | 252/49 |
| 3,356,773 | 12/1967 | Bacon et al. | 260/501.21 |
| 3,396,109 | 8/1968 | Butler et al. | 252/32.7 |
| 3,484,504 | 12/1969 | Cyba | 260/925 |
| 3,519,563 | 7/1970 | Lowe | 252/32.7 |
| 3,573,293 | 3/1971 | Wiese | 260/242 |
| 3,637,499 | 1/1972 | Pollak | 252/32.7 |
| 3,826,745 | 7/1974 | Ryer et al. | 252/32.7 |
| 3,926,821 | 12/1975 | Le Suer | 252/46.7 |
| 4,085,054 | 4/1978 | Bussi et al. | 252/49.3 |
| 4,101,427 | 7/1978 | Shaub | 252/32.7 |
| 4,154,779 | 5/1979 | Kruetzer | 260/924 |
| 4,215,002 | 7/1980 | Fein | 252/32.5 |
| 4,257,902 | 3/1981 | Singer | 252/8.5 |
| 4,329,249 | 5/1982 | Forsberg | 252/34.7 |
| 4,368,133 | 1/1983 | Forsberg | 252/75 |
| 4,721,802 | 1/1988 | Forsberg | 558/207 |

FOREIGN PATENT DOCUMENTS 1009914 11/1965 United Kingdom .
1044810 10/1966 United Kingdom .
1357745 6/1974 United Kingdom .

*Primary Examiner*—Anton H. Sutto
*Attorney, Agent, or Firm*—Robert A. Franks; Denis A. Polyn; Karl Bozicevic

[57] ABSTRACT

Phosphorus, sulfur and nitrogen containing salts prepared from dithiophosphorus compounds and amines are disclosed, which salts find utility in aqueous functional fluids. Compositions comprising a continuous aqueous phase, at least one of said salts prepared from dithiophosphorus compounds and amines and optionally a surface active agent are also disclosed.

13 Claims, No Drawings

AQUEOUS FLUIDS COMPOSITIONS CONTAINING DITHIOPHOSPHORUS/AMINE SALTS

CROSS-REFERENCE TO RELATED APPLICATION

This application is a division of Ser. No. 456,219 filed Jan. 7, 1983, now U.S. Pat. No. 4,721,802.

FIELD OF THE INVENTION

This invention relates to novel phosphorus, sulfur and nitrogen containing salts prepared from dithiophosphorus compounds and polyamines which salts are characterized by their anti-wear and extreme pressure properties. More particularly, this invention relates to novel phosphorus, sulfur and nitrogen containing salts prepared from dithiophosphorus acid selected from the group consisting of dithiophosphoric, dithiophosphinic and dithiophosphonic acid compounds and polyamines. This invention further relates to novel aqueous compositions for use as functional fluids for use in hydraulic and metal cutting applications comprising a continuous aqueous phase, a dithiophosphorus acid/amine salt and, optionally, a surface active agent.

BACKGROUND OF THE INVENTION

In recent times, efforts have been undertaken to develop water based functional fluids such as aqueous hydraulic and metal cutting fluids as replacements for the more conventional petroleum oil based functional fluids. As a result of these efforts, many different water based functional fluid systems have been developed for use as hydraulic and/or metal cutting fluids which provide certain advantages over the more conventional petroleum oil based fluids such as decreased fire hazards and health and environmental pollution problems.

Critical to the usefulness of such aqueous fluids in hydraulic and metal cutting applications is the fact that such aqueous fluids must possess the necessary anti-wear, extreme pressure and lubricity properties as found in more conventional petroleum oil based fluids. To impart such properties to aqueous fluids, many of the same anit-wear and extremem pressure additives employed in oil base fluids have also been employed to prepared these aqueous fluid systems. An example of an extremely effective class of anti-wear and extreme pressure additives that has been employed in both petroleum oil based and water based fluids is that consisting of phosphoric acid, thio- and dithiophosphoric acids and various derivatives thereof. For example, in U.S. Pat. No 3,320,164, there is disclosed a method for lubricating, cutting and cooling metal parts employing aqueous solutions containing, among others, reaction products of phosphoric, thiophosphoric and dithiophosphoric acids with aliphatic amines, polyamines, aliphatic amino ethers, aminoalcohols and etc. In U.S. Pat. No. 4,085,054, there is disclosed an aqueous metal working fluid comprising a solution in water of at least one alkali metal, ammonia or amine salt of an ortho-phosphoric ester containing chlorinated hydrocarbon and COOH containing hydrocarbon groups. U.S. Pat. No. 4,257,902 discloses substantially oil free aqueous industrial fluids which have included therein, among other additives, a functional additive such as a metal or amine salt of an organo sulfur, phosphorus, boron or carboxylic acid which is the same or of the same type as used in oil-based fluids. According to this patent, salts of thiophosphoric and dithiophosphoric acid and related acid esters are typical. Specific salts of these acids and esters, as disclosed in this patent, include the Group II metal salts such as zinc dicyclohexylphosphorodithioate and the zinc salts of a phosphorodithioate acid.

It is an object of the present invention to provide for a novel class of phosphorus, sulfur and nitrogen containing salts which salts possess anti-wear and extreme pressure properties. It is a further object of this invention to provide for anti-wear and extreme pressure salt compositions prepared from a dithiophosphoric, dithiophosphinic or dithiophosphonic acid compound and a polyamine. It is a further object of this invention to provide for novel aqueous (i.e. water based ) functional fluids such as hydraulic and metal cutting fluids containing such salts. In a broader aspect, it is a further object of this invention to provide novel aqueous functional fluids comprising a continuous aqueous phase, a dithiophosphorus acid/amine salt and, optionally, a surface active agent. These and other objects will become apparent to one of skill in the art as the description of the invention herein proceeds.

SUMMARY OF THE INVENTION

The present invention relates to novel phosphorus, sulfur and nitrogen containing salt compositions prepared from the reaction of (A) at least one dithiophosphorus acid compound selected from the group consisting of dithiophosphoric, dithiophosphinic and dithiophosphonic compounds of the formula

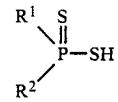

wherein $R^1$ and $R^2$ are individually selected from the group consisting of hydrocarbyl radicals containing from 1 to about 30 carbon atoms and hydrocarbyloxy radicals containing from 1 to about 30 carbon atoms, provided that when both $R^1$ and $R^2$ are hydrocarbyloxy radicals, at least one of said radicals is an aliphatic hydrocarbyloxy radical with (B) at least one polyamine selected from the group consisting of cyclic polyamines and alkylene polyamines of the formula

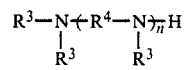

wherein n is an integer ranging from 1 to about 10; each of $R^3$ being individually selected from the group consisting of hydrogen atom, hydrocarbyl radicals containing from 1 to about 40 carbon atoms and hydroxy substituted hydrocarbyl radicals containing from 1 to about 40 carbon atoms and $R^4$ is a divalent hydrocarbyl radical containing from 1 to about 18 carbon atoms.

The present invention also relates to aqueous compositions comprising a continuous aqueous phase, (A) at least one phosphorus acid/amine salt prepared by reacting (I) at least one dithiophosphorus acid compound of the formula

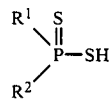

wherein $R^1$ and $R^2$ are individually selected from the group consisting of hydrocarbyl radicals containing from 1 to about 30 carbon atoms and hydrocarbyloxy radicals containing from 1 to about 30 carbon atoms with (II) at least one amino compound selected from the group consisting of cyclic polyamines and alkylene polyamines of the formula

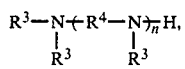

cyclic monoamines and monoamines of the formula

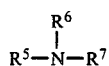

wherein each of $R^3$, $R^5$, $R^6$ and $R^7$ is individually selected from the group consisting of hydrogen atom, hydrocarbyl radicals containing from 1 to about 40 carbon atoms and hydroxy substituted hydrocarbyl radicals containing from 1 to about 40 carbon atoms provided however that at least one of $R^5$, $R^6$ and $R^7$ is said hydrocarbyl or hydroxy-substituted hydrocarbyl radical, $R^4$ is a divalent hydrocarbyl radical containing from 1 to about 8 carbon atoms and n is an integer ranging from 1 to about 10 and, optionally, (B) at least one surface active agent.

DETAILED DESCRIPTION OF THE INVENTION

The dithiophosphorus acid compounds, reactant (A), useful in preparing the novel dithiophosphorus acid/-polyamine salts of this invention and useful in preparing the aqueous compositions of this invention are those dithiophosphorus compounds selected from the group consisting of dithiophosphoric acid, dithiophosphinic and dithiophosphonic acid compounds of the formula

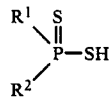

wherein $R^1$ and $R^2$ are individually selected from the group consisting of hydrocarbyl radicals containing from 1 to about 30 carbon atoms and hydrocarbyloxy radicals containing from 1 to about 30 carbon atoms. When $R^1$ and $R^2$ are both hydrocarbyloxy radicals and said dithiophosphorus acid compound is reacted with a polyamine to produce the novel salts of this invention, then at least one of said $R^1$ and $R^2$ will be an aliphatic hydrocarbyloxy radical.

When reference is made in this specification and the appended claims to hydrocarbyl, hydrocarbyloxy, hydrocarbon based, aliphatic hydrocarbyl, aliphatic hydrocarbyloxy aliphatic, alkyl, alkyloxy, alkylene and the like radicals, it is to be understood, unless expressly stated to the contrary, that reference is also being made to substantially hydrocarbyl, substantially hydrocarbyloxy, substantially hydrocarbon based, substantially aliphatic hydrocarbyl, substantially aliphatic hydrocarbyloxy, substantially aliphatic, substantially alkyl, substantially alkyloxy, substantially alkylene and the like radicals. The description of these radicals as being substantially hydrocarbyl means that they contain no non-hydrocarbyl substituents which would significantly affect the principal hydrocarbyl characteristics or properties of the radical relevant to their uses as described herein. Thus, it is obvious, for example, in the context of this invention, that a purely hydrocarbyl $C_{20}$ alkyl radical and a $C_{20}$ alkyl radical substituted with a methyl mercapto or methoxyl substituent at a point in the chain remote from other polar (i.e., nonhydrocarbyl) radicals, would be substantially similar in its properties with regard to its use in this invention, and would in fact be recognized as art equivalents by those of ordinary skill in the art. That is, one of ordinary skill in the art would recognize both such radicals to be substantially hydrocarbyl, etc.

Non-limiting examples of substituents which do not significantly alter the hydrocarbyl, etc., properties or nature of hydrocarbyl, etc., groups of this invention are the following:

Ether radicals (especially hydrocarbyloxy and particularly alkoxy groups of up to ten carbon atoms)

Amino radicals (including mono- and disubstituted aminos such as mono- and dialkyl amino or mono- and diaryl amino and the like, e.g., ethyl amino, dimethyl amino, diheptyl amino, cyclohexyl amino, benzyl amino, etc.)

Oxo radicals (e.g.,

such as in ketones and aldehydes)

Oxo radicals (e.g., —O— linkages in the main carbon chain)

Nitro radicals

Imino radicals (e.g.,

linkages in the main carbon chain)

Cyano radicals

Fluoro radicals

Chloro radicals

Thioether radicals (especially $C_{1-10}$ alkyl thioether)

Thia radicals (e.g., —S— linkages in the main carbon chain)

Carbohydrocarbyloxy radicals (e.g.,

hydrocarbyl)

Sulfonyl radicals

Sulfinyl radicals

This list is intended to be merely illustrative and not exhaustive and the omission of a certain class of substituent is not meant to require its exclusion.

In general, if such substituents are present, it will be found that not more than two of such substituents for each ten carbon atoms in the hydrocarbyl or hydrocarbyloxy radical and preferably not more than one of such substituents for each 10 carbon atoms, will not substantially affect the hydrocarbyl nature of the radicals. Nevertheless, the hydrocarbyl and hydrocarbyloxy radicals usually will be free from non-hydrocarbon groups due to economic considerations.

In the above formula, $R^1$ and $R^2$ can be saturated or unsaturated and include aliphatic hydrocarbyl radicals such as alkyl, alkenyl, cycloalkyl and cycloalkenyl; aromatic hydrocarbyl radicals; aliphatic and alicyclic substituted aromatic hydrocarbyl radicals; aromatic substituted aliphatic and alicyclic hydrocarbyl radicals and the like. $R^1$ and $R^2$ also include the analogous hydrocarbyloxy groups such as alkyloxy, alkenyloxy cycloalkyloxy, cycloalkenyloxy, aryloxy and the aliphatic and alicyclic substituted aryloxy and aromatic substituted aliphatic and cycloaliphatic oxy radicals. Suitable non-limiting representative examples of the hydrocarbyl groups represented by $R^1$ and $R^2$ above include methyl, ethyl, n-propyl, isopropyl, n-butyl, isobutyl, amyl, isoamyl, n-hexyl, 2-ethylhexyl, 4-methyl-2-pentyl, cyclohexyl, chlorocyclohexyl, methylcyclohexyl, heptyl, n-octyl, tertiary octyl, nonyl, lauryl, cetyl, phenyl, bromophenyl, 2,4-dichlorophenylethyl, chlorophenyl, nitrophenyl, methoxyphenyl, ethylphenyl, propylphenyl, butylphenyl, benzylphenylethyl, octenyl, cyclohexenyl, ethyl cyclopentyl, N,N'-dibutylamino propyl phenyl, 3-nitro octyl, p-carbothoxy phenyl, phenoxyphenyl, naphthyl, alkylated naphthyl such as propylene tetramersubstituted naphthyl, acetyl phenyl, 2-ethoxyethyl, 6-ethyl amino heptyl, 4-cyanophenyl, 3,3,3-trifluoropropyl, dichloromethyl 3-thia-n-octyl, 2-methyl mercapto naphthyl, 4-ethyl sulfonyl-n-butyl, 4-phenylsulfinyl phenyl, etc. Suitable non-limiting representative examples of the hydrocarbyloxy groups represented by $R^1$ and $R^2$ in the formula above include methyloxy, ethyloxy, n-propyloxy, isopropyloxy, n-butyloxy, amyloxy, n-hexyloxy, 2-ethylhexyloxy, 4-methyl-2-pentyloxy, cyclohexyloxy, chlorocyclohexyloxy, heptyloxy, n-octyloxy, isooctyloxy, tertiary octyloxy, nonyloxy, lauryloxy, cetyloxy, phenyloxy, bromophenyloxy, nitrophenyloxy, methoxy phenyloxy, ethylphenyloxy, propylphenyloxy, octenyloxy, cyclohexenyloxy, ethyl cyclopentyloxy, 3-nitro octyloxy, naphthyloxy, 2-ethoxyethyloxy, 6-ethyl amino heptyloxy, 4-cyanophenyloxy and the like hydrocarbyloxy radicals or groups. In a preferred embodiment, the radicals $R_1$ and $R_2$ are selected from the group consisting of aliphatic hydrocarbyl and aliphatic hydrocarbyloxy radicals or groups containing from 1 to about 20 carbon atoms and most preferred from 1 to about 18 carbons. In a most preferred embodiment, the radicals $R^1$ and $R^2$ are aliphatic hydrocarbyloxy radicals containing from 1 to about 20 carbon atoms and preferably from about 1 to about 18 carbon atoms. A particularly preferred dithiophosphorus compound is the dithiophosphoric acid ester, O,O-di(isooctyl)dithiophosphate.

Methods for the preparation of such phosphorus acid compounds are well known to those of skill in the art and do not need to be repeated here. For convenience, however, reference is made to the book "Organo-Phosphorus Compounds," by G. M. Kosolapoff, John Wiley Publishers, 1950, New York which is incorporated herein by reference for its disclosure of methods for preparing these phosphorus acid compounds.

As noted herein above, particularly preferred phosphorus acid compounds are the dithiophosphoric acid esters. These compounds can be prepared by the reaction of phosphorus pentasulfide, $P_2S_5$, or homologs thereof (e.g. $P_4S_{10}$) with hydroxyl containing compounds such as alcohols and phenols in which instance the radicals $R^1$ and $R^2$ in the formula above are hydrocarbyloxy radicals derived from the alcohol or phenol starting material. An example of this type of reaction is the reaction of phosphorus pentasulfide with isooctyl alcohol to produce O,O-di(isooctyl)dithiophosphate, which is the preferred phosphorus acid compound in preparing the salt compositions herein described and claimed. The reaction involves the use of four moles of alcohol per mole of phosphorus pentasulfide and reaction temperatures ranging from about 50° C. to about 200° C.

The amino compounds useful in preparing the novel phosphorus acid/polyamine salts of this invention and useful in preparing the aqueous compositions of this invention are those monoamines and polyamines selected from the group consisting of cyclic polyamines, alkylene polyamines of the formula

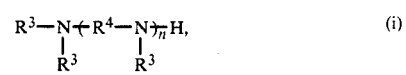

cyclic monoamines and monoamines of the formula

wherein each of $R^3$, $R^5$, $R^6$ and $R^7$ is individually selected from the group consisting of hydrogen atom, hydrocarbyl radicals containing from 1 to about 40 carbon atoms and hydroxy-substituted hydrocarbyl radicals containing from 1 to about 40 carbon atoms provided however that at least one of $R^5$, $R^6$ and $R^7$ is said hydrocarbyl or hydroxy-substituted hydrocarbyl radical, $R^4$ is a divalent hydrocarbon radical containing from 1 to about 18 carbon atoms and n is an integer from 1 to about 10.

Among the amino compounds useful in preparing certain salt compositions employed as component (A) of the aqueous compositions of this invention are monoamines. These monoamines can be primary, secondary or tertiary monoamines. The monoamines are generally substituted with hydrocarbyl radicals containing from 1 to about 40 carbon atoms. Generally these hydrocarbyl radicals are aliphatic radicals free from acetylenic unsaturation and contain from 1 to about 10 carbon atoms.

Among the monoamines useful in making the salts useful in this invention are those of the formula $HNR^8R^9$ wherein $R^8$ is an alkyl radical of up to 10 carbon atoms and $R^9$ is hydrogen atom or an alkyl radical of up to 10 carbon atoms. Other monoamines are aromatic monoamines of the general formula $HNR^{10}R^{11}$ wherein $R^{10}$ is a phenyl, alkylated phenyl, naphthyl or alkylated naphthyl radical of up to 10 carbon atoms and $R^{11}$ is a hydrogen atom, an alkyl radical of up to 10 carbon atoms, or a radical similar to $R^{10}$. Examples of suitable monoamines are ethylamine, diethylamine, n-butylamine, di-n-butylamine, allylamine, isobutylamine, cocoamine, stearylamine, laurylamine, methyllaurylamire, oleylamine, aniline, methylaniline, N-methylaniline, di-phenylamine, benzylamine, tolylamine and methyl-2-cyclohexylamine.

Hydroxy amines are also included in the class of useful monoamines. Such compounds are the hydroxy substituted hydrocarbyl analogs of the afore-described monoamines. Hydroxy monoamines useful in this invention have the formulas $HNR^{12}R^{13}$ and $HNR^{14}R^{15}$, wherein $R^{12}$ is an alkyl or hydroxy-substituted alkyl radical of up to 10 carbon atoms, $R^{13}$ is hydrogen atom or a radical similar to $R^{12}$, $R^{14}$ is a hydroxy-substituted phenyl, alkylated phenyl, naphthyl or alkylated naphthyl radical of up to 10 carbon atoms, and $R^{15}$ is hydrogen atom or a radical similar to $R^{14}$, at least one of $R^{12}$ and $R^{13}$ and at least one of $R^{14}$ and $R^{15}$ being hydroxy-substituted.

Suitable hydroxy-substituted monoamines include ethanolamine, di-3-propanolamine, 4-hydroxybutylamine, diethanolamine, N-methyl-2-propanolamine, 3-hydroxyaniline, triethanolamine, diethylethanolamine, dimethylethanolamine, tris(hydroxymethyl)methylamine and the like.

Cyclic monoamines are also useful in making the compositions of this invention. The cyclic ring can also incorporate unsaturation and can be substituted with hydrocarbyl radicals such as alkyl, alkenyl, aryl, alkaryl or aralkyl. In addition, the ring can also contain other hetero atoms such as oxygen, sulfur or other nitrogen atoms including those not having hydrogen atoms bonded to them. Generally, these rings have 3–10, preferably 5 or 6, ring members. Among such cyclic monoamines are aziridines, azetidines, azolidines, pyridines, pyrroles, piperidines, indoles, isoindoles, morpholines, thiamorpholines, azepines and tetrahydro-, dihydro- and perhydro-derivatives of each of the above.

The novel dithiophosphorus acid/amine salts of this invention, which salts are the preferred salts for use as component (B) of the aqueous compositions of this invention are those salts prepared from the dithiophosphorus acid compounds as described herein above with polyamines. Among the polyamines useful in preparing these novel and preferred salts are the alkylene polyamines including those of the formula

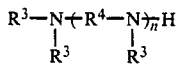

wherein n is an integer between about 1 and 10 and preferably between 2 and 8; each of $R^3$ being individually selected from the group consisting of hydrogen atom, hydrocarbyl radicals containing from 1 to about 40 carbon atoms and hydroxy substituted hydrocarbyl radicals containing from 1 to about 40 carbon atoms and $R^4$ is a divalent hydrocarbyl radical containing from 1 to about 18 carbon atoms. Preferably, each of $R^3$ is individually selected from the group consisting of hydrogen atom and aliphatic hydrocarbyl radicals containing from 1 to about 10 carbon atoms which aliphatic hydrocarbyl radicals may be substituted with 1 or 2 hydroxy groups and which aliphatic hydrocarbyl radicals may also contain ether linkages and wherein $R^4$ is a lower alkylene radical containing from 1 to about 10 and preferably from about 2 to about 6 carbon atoms. Especially preferred polyamines corresponding to the formula set forth hereinabove are the alkylene polyamines wherein each of the radicals $R^3$ is hydrogen. Such alkylene polyamines include methylene polyamines, ethylene polyamines, butylene polyamines, propylene polyamines, pentylene polyamines, etc. Cyclic polyamines such as piperazines and N-aminoalkyl substituted piperazines, N-aminoalkyl morpholines, N-aminoalkyl thiamorpholines, as well as polyether polyamines such as poly(oxyalkylene)polyamines are also included. Specific non-limiting representative examples of such polyamines are ethylenediamine, triethylenetetramine, tris-(2-aminoethyl)-amine, propylenediamine, trimethylenediamine, tripropylaminetetramine, tetraethylenepentamine, heptaethylenehexamine, N-aminopropylmorpholine, polyether polyamines such as those poly(oxyalkylene)polyamines commercially available from the BASF Wyandotte Corporation under the Trademark Tetronic ® Polyols and the like. A particularly useful polyamine for preparing the novel salt compositions preferred for use in the aqueous compositions of this invention is ethylenediamine.

Ethylene polyamines such as those mentioned hereinabove are described in detail under the heading Ethylene Amines in Kirk Othmer's "Encyclopedia of Chemical Technology" second edition, Vol. 7, pages 22–37, Inter Science Publishers, New York (1965). Such polyamines are most conveniently prepared by the reaction of ethylenedichloride with ammonia or by reaction of an ethylene imine with a ring opening reagent such as water, ammonia and etc. These reactions result in the production of a complex mixture of polyalkylene polyamines including cyclic condensation products such as the aforementioned piperazines. Such ethylene polyamine mixtures are useful in preparing the compositions of this invention. These mixtures are particularly useful in preparing the compositions of this invention. Satisfactory products can also be obtained by the use of pure ethylene polyamines.

Hydroxy polyamines, e.g., alkylene polyamines having one or more hydroxyalkyl substituents on the nitrogen atoms, are also useful in preparing the compositions of this invention. Generally the hydroxyalkyl-substituted alkylene polyamines are those in which the hydroxyalkyl group has less than about 10 carbon atoms. Examples of such hydroxyalkyl-substituted polyamines include N-(2-hydroxyethyl)-ethylene diamine, N,N'-bis(2-hydroxyethyl)ethylene diamine, 1-(2-hydroxyethyl)piperazine, monohydroxypropyl-substituted diethylene triamine, dihydroxypropyltetraethylene pentamine and N-(3-hydroxybutyl)tetramethylene diamine. Higher homologs obtained by condensation of the above-illustrated hydroxyalkyl-substituted alkylene amines through amino or hydroxy radicals are likewise useful.

Generally, formation of the salt compositions described herein is achieved by contacting 1.0 equivalent of the aforedescribed dithiophosphorus acid compounds (one equivalent of said acid compound being theoretically equal to its molecular weight) with from about 0.5 to about 2.0 equivalents of the aforedescribed monoamines or polyamines (one equivalent of such amines being theoretically equal to their molecular weight divided by the number of amine nitrogen atoms in said amines). Preferably the salt compositions will be prepared by contacting 1.0 equivalent of the acid compound with 1.0 to about 1.4 equivalents of the amine. The reaction is normally carried out for a minimum period of about one hour at temperatures ranging from ambient temperature up to but not exceeding the decomposition temperature of the desired salt product and generally not exceeding a temperature of about 75° C. Suitable, substantially inert organic liquid solvents or diluents may be used in the reaction and include such relatively low boiling liquids as hexane, heptane, benzene, toluene, xylene, methanol, isopropanol, etc., as well as high boiling materials such as solvent neutral oils, bright stocks and various types of synthetic and natural lubricating oil base stocks. Factors governing the choice and use of such materials are well known to those of skill in the art. Normally, such a diluent will be used to facilitate heat control, handling, filtration, etc. It is often desirable to select a diluent which will be compatible with the other materials, which are to be present in the environment where the product is intended to be used.

The following are non-limiting examples of general as well as specific and preferred embodiments of the invention. All references to percentages, parts and etc. in the present specification and appended claims refer to percentages, parts and etc. by weight unless expressly stated otherwise.

EXAMPLE 1

Into a two liter, four neck round bottom flask equipped with a stirrer, thermometer, and addition funnel is charged 111.2 grams diethylenetriamine (DETA). Seven hundred and ninety-five (795) grams of O,O'-diisooctylphosphorodithioic acid is then added drop wise to the DETA over a period of 1.5 hours. The reaction is exothermic and the rate addition of the acid is controlled such that the temperature does not exceed 75° C. After the addition is complete, external heat is applied to maintain the temperature at no greater than 75° C. for one hour. The resulting liquid is the product.

EXAMPLE 2

Employing the same equipment, temperature conditions and techniques of Example 1, a salt is prepared using 119.2 grams of tetraethylenepentamine and 842 grams of O,O'-diisooctylphosphorodithioic acid. Ninety-five (95) grams of an alcohol solution consisting of 61% isobutyl alcohol and 39% isoamyl alcohol is added to control viscosity.

EXAMPLE 3

Employing the same equipment, temperature conditions and techniques of Example 1, a salt is prepared using 91 grams of propylenediamine and 700 grams of O,O'-(4-methyl secondary amyl)-phosphorodithioic acid.

EXAMPLE 4

Employing the same equipment, temperature conditions and techniques of Example 1, a salt is prepared using 111.2 grams of diethylenetriamine and 808 grams of O,O'di(2-ethylhexyl)-phosphorodithioic acid.

EXAMPLE 5

Employing the same equipment, temperature conditions and techniques as Example 1, a salt is prepared using 79.5 grams of ethylenediamine and 808 grams of O,O'-di(2-ethylhexyl)-phosphorodithioic acid.

EXAMPLE 6

Employing the same equipment, temperature conditions and techniques of Example 1, a salt is prepared using 111.2 grams diethylenetriamine and 757 grams of di(iso-propylphenyl)phosphinodithioic acid.

EXAMPLE 7

Employing the same equipment, temperature conditions and techniques of Example 1, a salt is prepared using 79.5 grams ethylenediamine and 757 grams of di(isopropylphenyl)phosphinodithioic acid.

EXAMPLE 8

Employing the same equipment, temperature conditions and techniques of Example 1, a salt is prepared using 111.2 grams of diethylenetriamine and 732 grams of O-iso-octyl-o-xylylphosphonodithioic acid.

EXAMPLE 9

Employing the same equipment, temperature conditions and techniques of Example 1, a salt is prepared using 79.5 grams of ethylene diamine and 732 grams of O-isooctyl-o-xylylphosphonodithioic acid.

EXAMPLE 10

Employing the same equipment, temperature conditions and techniques of Example 1, a salt is prepared using 76 grams of ethylenediamine and 810 grams of O,O'-diisooctylphosphorodithioic acid.

EXAMPLE 11

Employing the same equipment, temperature conditions and techniques of Example 1, a salt is prepared using 91 grams of 1,2-propylenediamine and 790 grams of O,O'-diisooctylphosphorodithioic acid.

EXAMPLE 12

Employing the same equipment, temperature conditions and techniques as Example 1, a salt is prepared using 325 grams of Duomeen O an N-oleyl-1,3-propanediamine, available from Armak Company, and 701.3 grams of O,O'-diisooctylphosphorodithioic acid.

EXAMPLE 13

Employing the same equipment, temperature conditions and techniques as Example 1, a salt is prepared using 449.4 grams of Duomeen T an N-tallow-1,3-propanediamine, available from Armak Company, and 793 grams of O,O'-diisooctylphosphorodithioic acid.

EXAMPLE 14

Employing the same equipment, temperature conditions and techniques as Example 1, a salt is prepared using 170 grams of aminopropylmorpholine and 840 grams of O,O'-diisooctylphosphorodithioic acid.

EXAMPLE 15

Employing the same equipment, temperature conditions and techniques as Example 1, a salt is prepared using 567 grams of tertiary $C_{12-14}$ alkyl primary amine and 808 grams of O,O'-di(2-ethylhexyl)-phosphorodithioic acid.

EXAMPLE 16

Employing the same equipment, temperature conditions and techniques of Example 1, a salt is prepared using 552 grams of tertiary $C_{12-14}$ alkyl primary amine and 700 grams of O,O'-(4-methyl secondary amyl)-phosphorodithioic acid.

EXAMPLE 17

Employing the same equipment, temperature conditions and techniques of Example 1, a salt is prepared using 414.4 grams of Duomeen T, and 757 grams of di(isopropylphenyl)phosphinodithioic acid.

EXAMPLE 18

Employing the same equipment, temperature conditions and techniques of Example 1, a salt is prepared using 575 grams of tertiary $C_{12-14}$ primary alkyl amine and 757 grams of di(isopropylphenyl)phosphinodithioic acid.

EXAMPLE 19

Employing the same equipment, temperature conditions and techniques of Example 1, a salt is prepared using 184 grams of aminopropylmorpholine and 732 grams of O-isooctyl-o-xylylphosphonodithioic acid.

EXAMPLE 20

Employing the same equipment, temperature conditions and techniques of Example 1, a salt is prepared using 478 grams of Duomeen O, and 732 grams of O-isooctyl-o-xylylphosphonodithioic acid.

As noted hereinabove, the aqueous (i.e. water based) compositions of this invention are useful as aqueous hydraulic fluids, cutting fluids and the like. Generally, such aqueous fluids will comprise from about 60.0 to about 99.0 percent by weight, based on the total weight of the fluid, of water, from about 0.05 to about 10.0 percent by weight, based on the total weight of the fluid, of at least one salt composition as described herein and optionally from about 0.1 to about 25.0 percent by weight, based on the total weight of the fluid of at least one surface active agent. By the term surface active agent is meant any material which possesses the ability to stably maintain the salt compositions as described herein and which salt may be insoluble in the continuous water phase of the aqueous fluid, in said aqueous fluid. Generally, the salts useful in preparing the aqueous compositions of this invention are considered to be water soluble when at least one gram of salt can be dissolved in 100 milliliters of water at 25° C. If their solubility is less than this value, then a surface active agent will be employed in formulating the aqueous fluid. Such surface active agents, however, may also be employed even when said salts are water soluble to insure that they are stably maintained in the continuous water phase of the aqueous fluid. Surface active agents useful in preparing aqueous functional fluids containing the salts of this invention include emulsifiers, surfactants, detergents, dispersants and the like.

The types of surface active agents useful in preparing aqueous functional fluids based on the salt compositions of this invention are many and diverse and include surface active agents of the cationic, anionic, non-ionic and amphoteric type. Many such surface active agents of each type are known to the art. See, for example, McCutcheon's "Detergents and Emulsifiers", 1978, North American Edition, published by McCutcheon's Division, MC Publishing Corporation, Glen Rock, N.J., U.S.A., particularly parges 17-33 which are hereby incorporated by reference for their disclosures in this regard.

Of the non-ionic type of surface active agents useful in the aqueous compositions of this invention are the alkylene oxide-treated products, such as ethylene oxide-treated phenols, alcohols, esters, amines and amides. Ethylene oxide/propylene oxide block copolymers are also useful non-ionic surfactants and detergents. Glycerol esters and sugar esters are also known to be non-ionic surface active agents. A typical non-ionic class of surface active agent is the alkylene oxide-treated alkyl phenols such as the ethylene oxide alkyl phenol condensates sold by the Rohm & Haas Company. A specific example of these is Triton X-100 which contains an average of 9-10 ethylene oxide units per molecule, has an HLB value of about 13.5 and a molecular weight of about 628. Many other suitable non-ionic surface active agents are known; see, for example, the afore-mentioned McCutcheon's as well as the treatise "Non-ionic Surfactants" edited by Martin J. Schick, M. Drekker Co., New York, 1967, which is hereby incorporated by reference for its disclosures in this regard.

Cationic, anionic and amphoteric surface active agents can also be used in preparing aqueous compositions of this invention. Generally, these are all hydrophilic in nature. Anionic surface active agents contain negatively charged polar groups while cationic surface active agents contain positively charged polar groups. Amphoteric surface active agents contain both types of polar groups in the same molecule. A general survey of useful surface active agents is found in Kirk-Othmer Encyclopedia of Chemical Technology, Second Edition, Volume 19, page 507 and following (1969, John Wiley and Son, New York) and the aforementioned compilation published under the name of McCutcheon's. These references are both hereby incorporated by reference for their disclosures relating to such cationic, amphoteric and anionic surface active agents.

Among the useful anionic surface active agents are the widely known metal, amine and ammonium carboxylates, organo sulfates, sulfonates, sulfocarboxylates and phosphates. Useful cationic surface active agents include nitrogen compounds such as amine oxides and the well known quaternary ammonium salts. Amphoteric surface active agents include amino acid type materials and similar types. Various cationic, anionic and amphoteric surface active agents are available from the industry, particularly from such companies as Rohm and Haas and Union Carbide Corporation. Further information about anionic and cationic surface active agents also can be found in the texts "Anionic Surfactants", Parts II and III, edited by W.M. Linfield, published by Marcel Dekker, Inc., New York, 1976 and "Cationic Surfactants", edited by E. Jungermann, Marcel Dekker, Inc., New York, 1976. Both of these references are incorporated by reference for their disclosures in this regard.

A further type of surface active agent useful in this invention is that described in commonly assigned U.S. Pat. No. 4,368,133 and comprising nitrogen-containing, phosphorus free carboxylic acid derivatives made by reacting at least one carboxylic acid acylating agent with at least one alkanol tertiary amine. As disclosed in this patent, typical acylating agents useful in preparing such surface active agents are substitued succinic acids and derivatives thereof, e.g. anhydrides, wherein the substituent is a hydrocarbyl radical containing from about 20 to about 500 carbon atoms. Preferably the acylating agent is one wherein the hydrocarbyl substituent is an alkyl or alkenyl group of about 12, often about 30 to about 500 and preferably to about 300 carbon atoms. Amines useful for reacting with the hydrocarbyl substituted acylating agents to form the product are described as including monoamines and polyamines having at least one hydroxy group per molecule and normally up to about 40 carbon atoms.

The reaction between the acylating agent and the hydroxy-substituted hydrocarbyl amine or polyamine is carried out at temperatures ranging from about 30° C. to the composition temperature of the reaction product. Often the reaction is carried out under conditions such that the surface active agent is either an ester, salt, imide or amide or mixtures thereof.

The products described in this U.S. Pat. No. 4,368,133 are disclosed as having utility for incorporating functional additives such as metal salts of acid phosphates into water based functional fluids such as water-based hydraulic fluids. They have now also been found to operate in a similar manner in stably maintaining in the aqueous functional fluids of this invention the salt compositions described hereinabove. Therefore, the relevant teachings of U.S. Pat. No. 4,368,133 relating to the nitrogen containing, carboxylic acid products and their uses as described therein are hereby incorporated by reference.

Further examples of useful surface active agents include succinic acid esters and phosphatides such as those described in U.S. Pat. No. 3,281,356 which patent is herein incorporated by reference for its relevant disclosures in regard to such esters and phosphatides. A particularly useful phosphatide is soybean lecithin which is described in detail in "Encyclopedia of Chemical Technology," Kirk-Othmer, Vol. 8, pages 309–326 (1952).

The above surface active agents can also be employed in conjunction with a coupling agent to further improve the stabilizing ability of said surface active agents. Among the many diverse coupling agents which can be employed in combination with the above-described surface active agents are the aliphatic glycols. These aliphatic glycols may be polyalkylene glycols, preferably those in which the alkylene radical is a lower alkylene radical having from 1 to about 10 carbon atoms. Such alkylene glycols are illustrated by ethylene glycol, trimethylene glycol, 1,2-butylene glycol, 2,3-butylene glycol, tetramethylene glycol, hexamethylene glycol, or the like. Specific examples of the ethers include monophenyl ether of ethylene glycol, mono-(heptylphenyl)-ether of triethylene glycol, mono-alpha-octyl-beta-naphthyl ether of tetrapropylene glycol, mono-(polyisobutene[molecular weight of 1000]substituted phenyl) ether of octapropylene glycol, and mono-(o,p-dibutylphenyl) ether of polybutylene glycol, mono-(heptylphenyl) ether of trimethylene glycol and mono-(3,5-dioctylphenyl) ether of tetra-trimethylene glycol, etc. The mono-aryl ethers are obtained by the condensation of a phenolic compound such as an alkylated phenol or naphthyl with one or more moles of an epoxide such as ethylene oxide, propylene oxide, trimethylene oxide, or 2,3-hexylene oxide. The condensation is promoted by a basic catalyst such as an alkali or alkaline earth metal hydroxide, alcoholate, or phenate. The temperature at which the condensation is carried out may be varied within wide ranges such as from room temperature to about 250° C. Ordinarily it is preferably 50°–150° C. More than one mole of the epoxide may condense with the phenolic compound so that the product may contain in its molecular structure one or more of the radicals derived from the epoxide. A polar-substituted alkylene oxide such as epichlorohydrin or epibromohydrin likewise is useful to prepare the mono-aryl ether product and such product likewise is a useful surface active agent for stably suspending or dispersing water insoluble salts of this invention in aqueous fluids.

Likewise useful coupling agents are the mono-alkyl ethers of the aliphatic glycols in which the alkyl radical is, e.g., octyl, nonyl, dodecyl, behenyl, etc. The fatty acid esters of the mono-aryl or mono-alkyl ethers of aliphatic glycols also are useful. The fatty acids include e.g., oleic acid, stearic acid, iso-stearic acid, linolenic acid, linoleic as well as commercial acid mixtures such as are obtained by the hydrolysis of tall oils, sperm oils, etc. Specific examples are the oleate of mono-(heptylphenyl)ether of tetraethylene glycol and the acetate of mono-(polypropene[having molecular weight of 1000]-substituted phenyl) ether of tri-propylene glycol.

While aqueous fluids based on the salt compositions described hereinabove exhibit good extreme pressure, anti-wear and load carrying properties, it may sometimes be desirable to incorporate one or more additional agents to supplement this action. Such supplemental agents may be illustrated by the lead, nickel, molybdenum or Group IIA and IIB metal phosphorodithioate salts in which the metal may be magnesium, calcium, barium, strontium, zinc, cadmium, lead or nickel. Zinc phosphorodithioates are particularly preferred. Other types of extreme pressure agents which can find use in the aqueous compositions of this invention include chlorinated waxes, sulfurized or phosphosulfurized fatty acid esters, di- or trihydrocarbyl phosphites and phosphates, dihydrocarbon polysulfides and metal dithiocarbamates and carbamates. These and other useful extreme pressure agents are described in more detail in the books, both entitled "Lubricant Additives", by Smith and Smalheer (Published by the Lezius-Hiles Co., of Cleveland, Ohio) and by M. W. Raney (Published by the Noyes Data Corporation of Park Ridge, N.J.) pages 146–212, both of which are incorporated herein by reference for their disclosure of additional extreme pressure agents which can be used in conjunction with the salt compositions of the present invention.

Still another type of additive which can be useful in the aqueous fluids of the present invention is rust-inhibiting agents. One or more rust-inhibiting agents can be used. Effective rust-inhibiting agents are aliphatic amines (including hydroxy-substituted aliphatic amines), especially aliphatic primary amines having 1 to about 10 carbon atoms in the molecule. Other conventional rust-inhibiting agents can also be used either alone or in combination with the amines discussed above.

Other conventional types of rust-inhibiting agents are salts of aromatic acids, such as benzoic acid, etc., with the afore-described amines. Boric acid salts of the aliphatic amines such as those disclosed above are similarly useful.

The concentration of the rust-inhibitng agent in the aqueous fluids of this invention depend to some extent upon the relative concentration of water in the fluid. Ordinarily from about 0.1 part to 10.0 parts of rust-inhibiting agent per hundred parts of the aqueous fluid is sufficient.

The aqueous fluids of this invention may also contain a conventional foam inhibitor such as the silicon polymers, polyglycols, polyglycol esters and the like. Generally these foam inhibitors will be employed in the range of from about 0.01 to about 1.0 part per hundred parts of the aqueous fluid. Freezing point depressants (i.e., water-soluble polyhydric alcohols such as glycerol, ethylene glycol or other polar substances such as the methyl ether of diethylene glycol) are also useful. The concentration of these additives usually ranges from about 5 to about 50 parts per hundred parts of the aqueous fluid.

Anti-microbial agents (i.e. bactericides and fungicides) can also be included in the aqueous fluids of this invention. These are illustrated by the nitrobromo alkenes such as 3-nitro-1-propylbromide, nitrohydroxyalkanes, such as tris(hydroxymethyl)nitromethane, 2- nitro-2-ethyl-1,3-propanediol and 2-nitro-1-butanol and boric acid esters such as glycerol borate, triazines such as hexahydro-1-3-5-tris(2-hydroxyethyl)-s-triazine and the like. concentration of such bactericides usually range between about 0.001 to about 1 part per hundred parts of the aqueous fluid.

Oxidation inhibitors can also be included. Hindered phenols such as 2,4-di-t-pentyl phenol, and 2,6-di-t-octyl-4-secondary butyl phenol, are representative of useful oxidation inhibitors. The concentration of such oxidation inhibitors in aqueous fluids containing the salt compositions herein disclosed and claimed is usually between about 0.01 to about 2 parts per hundred parts of the aqueous fluid.

Generally the aqueous functional fluids can be prepared by direct addition of the salt and optional surface active agent, when required, to the aqueous phase, i.e. water, in any suitable blending device.

In addition to the aqueous fluids being prepared by direct addition of the salt and optional surface active agent to the aqueous phase, they may also be prepared from preformed aqueous concentrates, i.e. concentrates containing at least about 40% by weight water with the remainder being a combination of the salt, optional surface active agent and any additional additive materials such as described hereinabove and up to 50 percent by weight of a hydrocarbon oil, as well as substantially non-aqueous concentrates containing less than 40% by weight of water. Generally, when using aqueous concentrates to prepare the final aqueous fluid, such concentrates will contain from about 40% by weight to about 70% by weight of water and preferably from about 40% by weight to about 65% by weight of water. The substantially non-aqueous concentrates are analogous to the aforedescribed aqueous concentrates except that they contain less water (i.e. less than 40% by weight) and proportionally more of the other ingredients including the hydrocarbon oil.

Hydrocarbon oils that may be employed in preparing preformed non-aqueous concentrates as described hereinabove include those oils having a viscosity from about 40 SUS (Saybolt Universal Seconds) at 40° C. to about 500 SUS at 100° C. Mineral oils having lubricating viscosities, e.g. SAE 10 to 90 and preferably SAE 50 to 90 grade oils according to the standards set forth by the Society of Automotive Engineers, are especially advantageous. Mixtures of oils are similarly useful. Such mixtures are available from mineral oils, animal oils, syntnetic oils of the silicone type, synthetic oils of the polyolefin type and the like.

In addition to the use of aqueous and non-aqueous concentrates in preparing aqueous functional fluids based on the use of the salts described herein, concentrates comprising only the salt and optional surface active agent plus any additional additive materials such as those described hereinabove may also be used. Typical of such concentrates are the substantially water free and oil free concentrates containing from about 5.0% to about 80.0% by weight of the salt, from about 10 to about 95% by weight of the optional surface active agent and from about 0 to about 50.0% by weight of any additional additive materials.

When preparing the aqueous functional fluids of this invention from concentrates, such as those described immediately above, such preparation is effected by diluting the concentrates with water wherein the ratio of water to concentrate is in the range of from about 50:50 to about 99:1 by weight.

The aqueous compositions of this invention, in addition to being based substantially on water, can also be based on water-glycol mixtures.

Such compositions usually comprise water as a solvent, flame retarder, a water-soluble organic polymer thickener such as a polyoxyethylene polymer or an acrylate/methacrylate ester polymer, a water-miscible freezing point depressant, and small amounts of such additives as the afore-described anti-rust agents, oxidation inhibitors, and so on, as well as the salts of this invention and optional surface active agents as described herein. The water-miscible freezing point depressant is usually a common glycol or glycol ether having from about 2 to 14 carbon atoms such as ethylene glycol, diethylene glycol, triethylene glycol, ethylene glycol ethers, such as ethyl, methyl, propyl and butyl ethers thereof and similar ethers of diethylene glycol and triethylene glycol. In general, it is preferred to use simpler compounds such as represented by ethylene glycol, propylene glycol, butylene glycol, and diethylene glycol for they are cheap, easily obtainable and blend readily with water to give very low freezing point mixtures.

Usually, the water content of such water-glycol mixtures is limited to a maximum of about 50 percent to be free from freezing problems. The minimum amount of water is usually 10 percent also to avoid excessively high freezing points of the composition.

The preferred thickeners for use in these compositions are soluble organic polymeric compounds usually copolymers of ethylene oxide and 1,2-propylene or 1,3-propylene oxide. A preferred one is one containing about 75 mole percent ethylene oxide and about 25 mole percent of propylene oxide, copolymerized to a thick fluid polymer having a number average molecular weight of about and not in excess of 15,000 to 20,000. Such polymers have viscosities of about 50,000 to about 100,000 SUS at 100° F. Blends of such polymers may be used to achieve specific purposes. All of the afore-described additives which are used in the water based fluids can be used in appropriate circumstances in the water-glycol fluids. Usually solubility and compatibility dictate the choice of such additives which is within the skill of those skilled in the art.

The following examples are illustrative of the preparation of water-based concentrates and functional fluids of this invention. Again, such examples are intended to be representative only and are not to limit the invention herein described in any manner. All references to percentages, parts and etc. as employed in these examples refers to percentages, parts and etc. by weight unless expressly stated otherwise

EXAMPLES 21–28

A series of concentrate solutions is prepared in accordance with the following procedure: to a round bottom flask, fitted with a stirrer and thermowell is charged the reaction product of polyisobutenyl succinic anhydride and diethylethanolamine, solvent refined 100 neutral oil, and diethylamine. The contents are heated to and stirred at 40° C. Unitol DT-40, a tall oil fatty acid available from Union Camp is slowly added to the contents of the flask. The reaction is exothermic and the temperature increased to 50° C. A number of the dithiophosphorus acid/amine salts prepared above are charged, and the temperature is maintained at 50°–60° C. for one hour. External heating is discontinued and tap water is charged over a period of one hour. Then added is dimethylethanolamine, diethylethanolamine, and Dow DB-110A, a defoamer from Dow Chemical. The contents are mixed an additional 15 minutes to give the concentrate. Pertinent information relating to the compositional make-up of the various concentrates comprising this series is given in Table I below.

|  | Example Number | | | | | | | |
|---|---|---|---|---|---|---|---|---|
|  | 21 | 22 | 23 | 24 | 25 | 26 | 27 | 28 |
| LUBRIZOL 5603[1] | 19.85 | 19.87 | 19.85 |  | 19.85 | 16.00 |  | 17.00 |
| LUBRIZOL 5602[1] |  |  |  | 19.85 |  |  | 19.65 |  |
| Solvent refined 100 neutral | 1.95 | 1.93 | 1.95 | 1.95 | 6.95 | 8.00 | 6.88 | 10.00 |
| Diethyl amine | 1.63 | 1.60 | 1.63 | 1.63 | 1.63 | 1.58 | 1.61 | 1.46 |
| Unitol DT-40[2] | 5.06 | 5.06 | 5.06 | 5.06 | 5.06 | 4.91 | 5.00 | 4.53 |
| DB-110A[3] | 1.00 | 1.00 | 1.00 | 1.00 |  |  | .99 |  |
| Water | 56.06 | 56.10 | 56.06 | 56.06 | 52.06 | 55.50 | 52.03 | 53.00 |
| Dimethylethanol amine | 2.00 | 2.00 | 2.00 | 2.00 | 2.00 | 2.00 | 1.98 | 2.00 |
| Diethylethanol amine | 2.50 | 2.50 | 2.50 | 2.50 | 2.50 | 2.00 | 1.98 | 2.00 |
| Product of Example No. 11 | 9.95 |  |  |  |  |  |  |  |
| Product of Example No. 1 |  | 9.93 |  |  |  |  |  |  |
| Product of Example No. 10 |  |  | 9.95 | 9.95 | 9.95 | 10.00 | 9.85 | 10.00 |

[1]Aqueous dispersants available from The Lubrizol Corporation.
[2]Tall oil fatty acid from Union Camp.
[3]Defoamer from Dow Chemical.

The following examples are illustrative of water-based fluids of the present invention derived from the concentrates prepared above.

EXAMPLES 29–31

To a one neck glass vessel is charged water and and various of the concentrates prepared above. The material is mixed well to give the desired final fluid. All values for the amount of water and concentrate employed to prepare the final fluids are given on the basis of percent by weight based on the total weight of the final fluid. Table II contains all pertinent data relating to the compositions prepared in these examples.

TABLE II

| Component | Example Number | | |
|---|---|---|---|
|  | 29 | 30 | 31 |
| Water | 95 | 95 | 95 |
| Product of Example 23 | 5 | — | — |
| Product of Example 27 | — | 5 | — |
| Product of Example 22 | — | — | 5 |

What is claimed is:

1. A composition comprising an aqueous fluid and a salt prepared by reacting (A) at least one dithiophosphorus acid compound of the formula

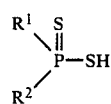

wherein $R^1$ and $R^2$ are individually selected from the group consisting of hydrocarbyl radicals containing from 1 to about 30 carbon atoms and hydrocarbyloxy radicals containing from 1 to about 30 carbon atoms, provided that when both $R^1$ and $R^2$ are hydrocarbyloxy radicals, at least one of said radicals is an aliphatic hydrocarbyloxy radical with (B) at least one polyamine selected from the group consisting of cyclic polyamines and alkylene polyamines of the formula

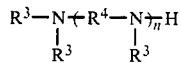

wherein n is an integer ranging from 1 to about 10; each of $R^3$ being individually selected from the group consisting of hydrogen atom, hydrocarbyl radicals containing from 1 to about 40 carbon atoms and hydroxy substituted hydrocarbyl radicals containing from 1 to about 40 carbon atoms and $R^4$ is a divalent hydrocarbon based radical containing from 1 to about 18 carbon atoms.

2. A composition according to claim 1 wherein (A) is a dithiophosphorus compound in which $R^1$ and $R^2$ are individually selected from the group consisting of hydrocarbyl radicals containing from 1 to about 20 carbon atoms and hydrocarbyloxy radicals containing from 1 to about 20 carbon atoms.

3. A composition according to claim 2 wherein (A) is a dithiophosphorus compound in which both $R^1$ and $R^2$ are hydrocarbyloxy radicals containing from 1 to about 18 carbon atoms.

4. The composition of claim 3 wherein both $R^1$ and $R^2$ are aliphatic hydrocarbyloxy radicals.

5. The composition of claim 4 wherein both $R^1$ and $R^2$ are alkyloxy radicals.

6. A composition according to claim 1 wherein (B) is an alkylene polyamine in which n is an integer ranging from 1 to about 8 carbon atoms, each of $R^3$ is individually selected from the group consisting of hydrogen, alkyl radicals containing from 1 to about 10 carbon atoms and hydroxy substituted alkyl radicals containing from 1 to about 10 carbon atoms and $R^4$ is a lower alkylene radical containing from 1 to about 10 carbon atoms.

7. A composition according to claim 6 wherein n is an integer ranging from 1 to about 4; each of $R^3$ is hydrogen and $R^4$ is a lower alkylene radical containing from 2 to about 6 carbon atoms.

8. A composition comprising an aqueous fluid and the salt prepared by reacting (A) at least one dithiophosphorus compound of the formula

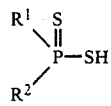

wherein $R^1$ and $R^2$ are both the same or different hydrocarbyloxy radicals containing from 1 to about 18 carbon atoms provided that at least one of said radicals $R^1$ and $R^2$ is an aliphatic hydrocarbyloxy radical with (B) at least one alkylene polyamine of the formula

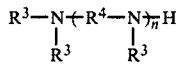

wherein n is an integer ranging from 1 to about 8, each of $R^3$ is individually selected from the group consisting of hydrogen, alkyl radicals containing from 1 to about 10 carbon atoms and hydroxy substituted alkyl radicals containing from 1 to about 10 carbon atoms and $R^4$ is a lower alkylene radical containing from 1 to about 10 carbon atoms.

9. The composition of claim 8 wherein both $R^1$ and $R^2$ are aliphatic hydrocarbyloxy radicals.

10. The composition of claim 9 wherein both $R^1$ and $R^2$ are alkyloxy radicals.

11. The composition of claim 8 wherein n is an integer ranging from 1 to about 4; each of $R^3$ is hydrogen and $R^4$ is a lower alkylene radical containing from 2 to about 6 carbon atoms.

12. The composition of claim 11 wherein both $R^1$ and $R^2$ are aliphatic hydrocarbyloxy radicals.

13. The composition of claim 12 wherein both $R^1$ and $R^2$ are alkyloxy radicals.

* * * * *

UNITED STATES PATENT AND TRADEMARK OFFICE
CERTIFICATE OF CORRECTION

PATENT NO. : 4,774,351
DATED : September 27, 1988
INVENTOR(S) : John Wesley Forsberg It is certified that error appears in the above-identified patent and that said Letters Patent is hereby corrected as shown below:

Insert on the cover page, following the line identifying the assignee:

[*] Notice: The portion of the term of this patent subsequent to Jan. 26, 2005 has been disclaimed.

Column 15, bridging lines 48 and 49, change "syntnetic" to -- synthetic --.

Signed and Sealed this

Twenty-third Day of May, 1989

Attest:

DONALD J. QUIGG

*Attesting Officer*  *Commissioner of Patents and Trademarks*